(12) United States Patent
Mink et al.

(10) Patent No.: US 7,423,162 B2
(45) Date of Patent: Sep. 9, 2008

(54) PROCESS FOR THE PREPARATION OF (4-HYDROXY-6-OXO-TETRAHYDROPYRAN-2-YL) ACETONITRILE AND DERIVATIVES

(75) Inventors: Daniel Mink, Eupen (BE); Wilhelmus Hubertus Joseph Boesten, Sittard (NL); Michael Wolberg, Neutraubling (DE); Natascha Sereinig, Eindhoven (NL)

(73) Assignee: DSM IP Assets B.V., Te Heerlen (NL)

( * ) Notice: Subject to any disclaimer, the term of this patent is extended or adjusted under 35 U.S.C. 154(b) by 154 days.

(21) Appl. No.: 10/554,294

(22) PCT Filed: Apr. 28, 2004

(86) PCT No.: PCT/NL2004/000284

§ 371 (c)(1),
(2), (4) Date: Jul. 6, 2006

(87) PCT Pub. No.: WO2004/096788

PCT Pub. Date: Nov. 11, 2004

(65) Prior Publication Data

US 2006/0258733 A1    Nov. 16, 2006

(30) Foreign Application Priority Data

May 2, 2003    (EP) .................................. 03101227

(51) Int. Cl.
*C07D 309/30*    (2006.01)
(52) U.S. Cl. ...................................... 549/292
(58) Field of Classification Search ................... 549/292
See application file for complete search history.

(56) References Cited

U.S. PATENT DOCUMENTS

2005/0153407 A1 * 7/2005 Greenberg et al. .......... 435/135

FOREIGN PATENT DOCUMENTS

| WO | WO 89/07598 | 8/1989 |
|----|-------------|--------|
| WO | WO 02/06266 | 1/2002 |

OTHER PUBLICATIONS

Kelvin L. Baumann et al; "The Convergent Synthesis of CI-981, an Optically Active, Highly Potent, Tissue Selective Inhibitor of HMG-CoA Reductase"; Tetrahedron Letters, vol. 33, No. 17, pp. 2283-2284; 1992.

Peter W.K. Woo et al; Atorvastatin, An HMG-COA Reductase Inhibitor and Effective Lipid-Regulating Agent—Part III [1a,b] Syntheses of [$^2$H$_5$]-,[$^{13}$C$_B$], and [$^{13}$C$_7$, $^{15}$N] Atorvastatin and Their Application in Metabolic and Pharmacokinetic Studies; Journal of Labelled Compounds and Radiopharmaceuticals J. Labelled Cpd. Radiopharm. 42, 135-145; (1999).

Philip L. Brower et al; "The Synthesis of (4R-cis)-1,1-Dimethylethyl 6-cyanomethyl-2,2-dimethyl-1,3-dioxane-4-acetate, a Key Intermediate for the Preparation of CI-981, A Highly Potent, Tissue Selective Inhibitor of HMG-CoA Reductase"; Tetrahedron Letters, vol. 33, No. 17; pp. 2279-1182; 1992.

William A. Greenberg et al; "Developmen f an Efficient, Scalable, Aldolase-Catalyzed Process for Enantioselective Synthesis of Statin Intermediates"; PNAS, Apr. 20, 2004; vol. 101, No. 16, pp. 5788-5793.

* cited by examiner

*Primary Examiner*—Bernard Dentz
(74) *Attorney, Agent, or Firm*—Nixon & Vanderhye P.C.

(57) ABSTRACT

The invention relates to a process for the preparation of (4-hydroxy-6-oxo-tetrahydro-pyran-2-yl)-acetonitrile from 6-X-substituted-methyl-4-hydroxy-tetrahydro-pyran-2-one, wherein X stands for a leaving group, by reacting 6-X-substituted-methyl-4-hydroxy-tetrahydro-pyran-2-one with a cyanide ion in water and by subsequent lowering of the pH to a pH between 0 and 5. (4-hydroxy-6-oxo-tetrahydro-pyran-2-yl)-acetonitrile and other compounds obtainable from (4-hydroxy-6-oxo-tetrahydro-pyran-2-yl)-acetonitrile may suitably be used in the preparation of a pharmaceutical preparation, more in particular in the preparation of statins, more in particular in the preparation of Atorvastatine or a salt thereof, for instance its calcium salt. The invention also relates to (4-hydroxy-6-oxo-tetrahydro-pyran-2-yl)-acetonitrile and other compounds obtainable therefrom.

15 Claims, No Drawings

PROCESS FOR THE PREPARATION OF (4-HYDROXY-6-OXO-TETRAHYDROPYRAN-2-YL) ACETONITRILE AND DERIVATIVES

This application is the US national phase of international application PCT/NL2004/000284 filed 28 Apr. 2004 which designated the U.S. and claims benefit of EP 03101227.1, dated 2 May 2003, the entire content of which is hereby incorporated by reference.

The invention relates to a process for the preparation of a compound of formula 1

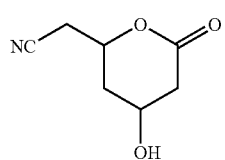

The compound mentioned above can suitably be used as an intermediate in the preparation of several active ingredients of pharmaceuticals, in particular in the preparation of HMG-CoA reductase inhibitors, more in particular in the preparation of statins, for example in the preparation of Atorvastatin as described by A. Kleemann, J. Engel; pharmaceutical substances, synthesis, patents, applications 4th edition, 2001 Georg Thieme Verlag, p. 146-150.

The compound of formula 1 is prepared according to the invention by reacting a compound of formula 2

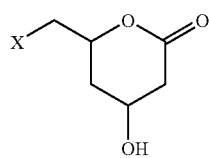

wherein X stands for a leaving group with a cyanide ion in water and by subsequent lowering of the pH to a pH between 0 and 5.

Compared to the known processes to Atorvastatin, the process of the invention is a facile process which process is also efficient and cost-effective. Advantages of the present process are for example that it is well upscaleable, does not require for instance ultralow temperature or hazardous reagents like metalorganics or alkylboranes.

Leaving groups X, which can be used in this reaction include for example halogens, in particular Cl, Br, I; sulfonic acid ester groups, in particular tosylate, mesylate or benzene sulfonate groups, each of which may optionally be substituted with a nitro or a halogen group; acyloxy groups, in particular acetoxy or benzoyloxy groups. For practical reasons, X preferably stands for Cl.

For the above reaction, cyanide ions may, for example, be added to the reaction in the form of cyanide salts or as a combination of HCN and a base. In principle all cyanide salts known to the skilled person, may be used. Examples of cyanide salts include: cyanide salts with an alkalimetal as a cation, for example sodium cyanide, potassium cyanide or lithium cyanide; cyanide salts with a bulky cation, for example tetrabutylammonium cyanide or tetrabutyl phosphonium cyanide. For commercial use, sodium cyanide or potassium cyanide is preferred.

Preferably the concentration of the cyanide ions is at least 1 mole per litre, more preferably at least 5 moles per litre and most preferably at least 10 moles per litre. The concentration of the cyanide ions is preferably chosen as high as possible.

The temperature of the reaction is in principle not critical, for example temperatures may be chosen between 0 and 100° C., preferably between 30 and 70° C., more preferably between 40 and 60° C.

Lowering of the pH to a pH between 0 and 5, preferably between 2 and 4 can be done according to a manner known per se, for example by the addition of an acid, preferably a strong acid, for instance with a pKa<4, preferably with a $PK_a<2$.

If desired, before lowering of the pH, excess cyanide ions may be removed by oxidation with an oxidizing agent, for example with chlorine, with hypochlorite or with $H_2O_2$, for example as described in U.S. Pat. No. 3,617,567.

In a different embodiment of the invention, the compound of formula 2 may first be treated with a base prior to being reacted with a cyanide ion. Both reaction steps may be performed in the same reaction vessel.

The choice of base used in the conversion of the compound of formula 2 into a compound of formula 1, either in combination with HCN or prior to the reaction with a cyanide ion, is in principle not critical. Examples of bases which may suitably be used include: alkali (earth) metal hydroxides, e.g. sodium or potassium hydroxide, alkali (earth) metal carbonates, e.g. sodium carbonate or magnesium carbonate, $NH_4OH$ or $N(alkyl)_4OH$, alcoholates, $NH_3$ or $N(alkyl)_3$ and carboxylates. The base is preferably used in a molar ratio of between 0.3 and 3 as compared to the amount of compound of formula 2, more preferably in a molar ratio between 0.5 and 1.5, most preferably in a molar ratio between 0.9 and 1.1. If the compound of formula 2 is first treated with a base, the molar ratio between the total quantity of cyanide ion and the total quantity of compound of formula 2, is preferably between 0.5 and 10, more preferably between 1 and 5, most preferably between 1.5 and 2.5.

If the compound of formula 2 is not first treated with a base, preferably, the molar ratio between the total quantity of cyanide ion and the total quantity of compound of formula 2, is between 1 and 11, more preferably between 2 and 6, most preferably between 2.5 and 3.5 molar equivalents.

The compound of formula 1 may be reduced with a suitable reducing agent to form the corresponding compound of formula 3:

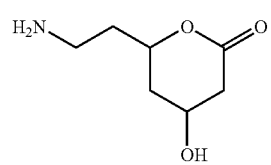

The reducing agent may be chosen from the group of reducing agents that is generally known to be applicable in the reduction of a nitrile to an amine. Examples of reducing agents include hydride reducing agents, for example dibalH (di isobutylaluminiumhydride); hydrogen reducing agents, for example Raney nickel with $H_2$, $Rh/Al_2O_3/NH_2$ or $Pd(OH)_2$ with $H_2$.

The compound of formula 2, wherein X stands for a leaving group may, for example, be prepared by an aldol condensation between acetaldehyde and an aldehyde which is substituted on the 2-position by X, wherein X is as defined above, in the presence of an aldolase, for example as described in U.S. Pat. No. 5,795,749 and by subsequent reaction of the formed compound of formula 4,

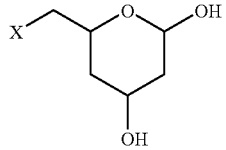

(4)

wherein X is as defined, above with an oxidizing agent.

Preferably, in the aldol condensation for the preparation of a compound of formula 4, the carbonyl concentration,—the sum of the concentration of aldehyde, 2-substituted aldehyde and the intermediate product formed in the reaction between the aldehyde and the 2-substituted aldehyde (a 4-substituted-3-hydroxybutanal intermediate)—, is between 0.1 and 5 moles per litre of the reaction mixture, more preferably between 0.6 and 4 moles per litre of the reaction mixture.

The reaction temperature and the pH are not critical and both are chosen as a function of the substrate. Preferably the reaction is carried out in the liquid phase. The reaction can be carried out for example at a reaction temperature between −5 and 45° C., preferably between 0 and 10° C. and a pH between 5.5 and 9, preferably between 6 and 8.

The reaction is preferably carried out at more or less constant pH, use for example being made of a buffer or of automatic titration. As a buffer for example sodium and potassium bicarbonate, sodium and potassium phosphate, triethanolamine/HCl, bis-tris-propane/HCl and HEPES/KOH can be applied. Preferably a potassium or sodium bicarbonate buffer is applied, for example in a concentration between 20 and 400 mmoles/l of reaction mixture.

The molar ratio between the total quantity of aldehyde and the total quantity of 2-substituted aldehyde is not very critical and preferably lies between 1.5:1 and 4:1, in particular between 1.8:1 and 2.2:1.

Preferably the aldolase used is 2-deoxyribose-5-phosphate aldolase (DERA, EC 4.1.2.4) or a mutant hereof, more preferably DERA from *Escherichia coli* or a mutant hereof. The quantity of DERA to be used is not very critical and is chosen as a function of for example the reactants applied, the reactant concentrations, the desired reaction rate, the desired duration of the reaction and other economic factors. The quantity of DERA to be used lies between for example 50 and 5000 U/mmole of the substituted or unsubstituted aldehyde. 1 U (unit) is a measure of the enzymatic activity and corresponds to the conversion of 1 µmole of 2-deoxyribose-5-phosphate per minute at 37° C.

The process of the invention is especially advantageous since both the preparation of a compound of formula 2 from simple aldehydes and the subsequent conversion of the compound of formula 2 into a compound of formula 1 may be performed in water. The use of water as a solvent has many advantages known to the person skilled in the art, for example, water is a cheap, widely available and environmentally benign solvent.

As an oxidizing agent to be used in the oxidization of the compound of formula 4, in principle all oxidizing agents known to the skilled person to be applicable in the oxidation of an alcohol to a ketone can be applied. Examples of such oxidizing agents include: $Br_2$, $Cl_2$, $NaClO$, $NiO_4$, $CrO_3$ and peroxides, for example $H_2O_2$.

The compound of formula 1 or a compound of formula 3 may be subsequently converted into a compound of formula 6,

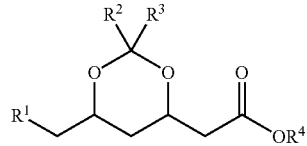

(6)

wherein $R^1$ stands for CN or $CH_2NH_2$ and $R^2$, $R^3$ and $R^4$ each independently stand for an alkyl with for instance 1 to 12 C-atoms, preferably 1-6 C-atoms, an alkenyl with for instance 1 to 12 C-atoms, preferably 1-6 C-atoms, a cycloalkyl with for instance 3-7 C-atoms, a cycloalkenyl with for instance 3-7 C-atoms, an aryl with for instance 6-10 C-atoms or an aralkyl with for instance 7 to 12 C-atoms, each of $R^2$, $R^3$ and $R^4$ may be substituted and wherein $R^2$ and $R^3$ may form a ring together with the C-atom to which they are bound, use being made of a suitable acetal forming agent, in the presence of an acid catalyst, for example as described in WO 02/06266.

The substituents on $R^2$, $R^3$ and $R^4$ are for example halogens or hydrocarbon groups with for instance 1-10 C-atoms, optionally containing one or more heteroatoms, for instance Si, N, P, O, S, F, Cl, Br or I.

The term alkyl refers to straight-chain as well as to branched saturated hydrocarbon chains. Examples of these are methyl, ethyl, n-propyl, i-propyl, n-butyl, t-butyl, hexyl and octyl. The term alkenyl relates to straight-chain and branched unsaturated hydrocarbon chains, like vinyl, allyl and i-butenyl. The term cycloalkyl comprises saturated ring-shaped hydrocarbon chains. Examples of these are cyclopentyl and cyclohexyl. The term cycloalkenyl refers to unsaturated ring-shaped hydrocarbon chains. The term aryl relates to aromatic and heteroaromatic systems, as well as substituted variants thereof. Examples of these are phenyl, p-methylphenyl, and furanyl. The term aralkyl means a combination of aryl and alkyl with the aryl residue connected via an alkyl chain, for example benzyl.

The groups $R^2$, $R^3$ and $R^4$ preferably each independently stand for a C 1-3 alkyl, more preferably methyl or ethyl. Preferably $R^4$ stands for methyl. In practice, $R^2=R^3=R^4$ is methyl is most preferred.

Examples of suitable acetal forming agents that can be applied in the process according to the invention include dialkoxypropane compounds, with the alkoxy groups each preferably having 1-3 carbon atoms, for instance 2,2-dimethoxypropane or 2,2-diethoxypropane; alkoxypropene, with the alkoxy group preferably having 1-3 carbon atoms, for instance 2-methoxypropene or 2-ethoxypropene. Most preferred is 2,2-dimethoxypropane. This can optionally be formed in situ from acetone and methanol, preferably with water being removed.

As acid catalyst use can be made of the acid catalysts known for acetal forming reactions, preferably organic strong acids, with a $pk_a<4$, with a non-nucleophilic anion, for example sulphonic acids, in particular p-toluene sulphonic acid, methane sulphonic acid or camphor sulphonic acid; or inorganic strong acids, with a $pk_a<4$, with a non-nucleophilic anion, for example sulphuric acid, HCl, phosphoric acid: acid ion exchangers, for example DOWEX; or solid acids, for example the so-called heteropolyacids.

The acetal formation can be carried out without using a separate solvent; if desired the reaction can also be carried out in an organic solvent. Examples of suitable organic solvents include ketones, in particular acetone, hydrocarbons, in particular aromatic hydrocarbons, for example toluene, chlorinated hydrocarbons, for example methylene chloride.

The temperature at which the acetal forming reaction is carried out is not critical and preferably lies between −20° C. and 150° C., in particular between 0° C. and 100° C.

The molar ratio of acetal forming agent to the compound of formula 5 preferably lies between 1:1 and 20:1, in particular between 3:1 and 5:1. Using an organic solvent the molar ratio is in particular between 1:1 and 2:1.

The molar ratio of acid catalyst to the compound of formula 5 preferably lies between 1:1 and 0.001:1, in particular between 0.05:1 and 0.1:1.

The compound of formula 6, wherein $R^1$ stands for CN or $CH_2NH_2$ and wherein $R^2$, $R^3$ and $R^4$ are as defined above may be subsequently hydrolysed in the presence of a base and water to form the corresponding salt of formula 7,

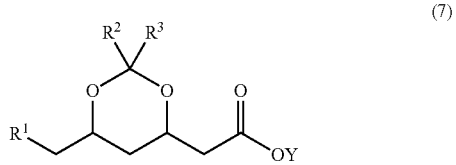

(7)

wherein Y stands for an alkali metal, for instance lithium, sodium, potassium, preferably sodium; an alkali earth metal, for instance magnesium or calcium, preferably calcium; or a substituted or unsubstituted ammonium group, preferably a tetraalkyl ammonium group. Optionally, the hydrolysis is followed by conversion to the corresponding compound of formula 7, wherein Y is H, for example as described in WO 02/06266.

The hydrolysis of the compound of formula 6 is preferably carried out with at least 1 base equivalent, in particular 1-1.5 base equivalents, relative to the compound of formula 6. In principle a larger excess can be used, but in practice this usually does not offer any advantages.

The reaction is preferably carried out at a temperature between −20° C. and 60° C., in particular between 0° C. and 30° C.

The hydrolysis can for example be carried out in water, an organic solvent, for example an alcohol, in particular methanol or ethanol, an aromatic hydrocarbon, for example toluene, or a ketone, in particular acetone or methyl isobutyl ketone (MIBK), or a mixture of an organic solvent and water, optionally catalysed by a phase transfer catalyst (PTC) or addition of a cosolvent.

The compound of formula 6, wherein $R^1$, $R^2$, $R^3$ and $R^4$ are as defined above may also be converted enzymatically to form the corresponding salt of formula 7, wherein $R^1$, $R^2$, $R^3$ and Y are as defined above, for example as described in WO 02/06266.

Examples of enzymes that can suitably be used in the conversion of a compound of formula 6 into the corresponding salt of formula 7 include enzymes with lipase or esterase activity, for example enzymes from *Pseudomonas*, in particular *Pseudomonas fluorescens, Pseudomonas fragi; Burkholderia*, for example *Burkholderia cepacia; Chromobacterium*, in particular *Chromobacterium viscosum; Bacillus*, in particular *Bacillus thermocatenulatus, Bacillus licheniformis; Alcaligenes*, in particular *Alcaligenes faecalis; Aspergillus*, in particular *Aspergillus niger; Candida*, in particular *Candida antarctica, Candida rugosa, Candida lipolytica, Candida cylindracea; Geotrichum*, in particular *Geotrichum candidum; Humicola*, in particular *Humicola lanuginosa; Penicillium*, in particular *Penicillium cyclopium, Penicillium roquefortii, Penicillium camembertii; Rhizomucor*, in particular *Rhizomucor javanicus, Rhizomucor miehei; Mucor*, in particular *Mucor javanicus; Rhizopus*, in particular *Rhizopus oryzae, Rhizopus arhizus, Rhizopus delemar, Rhizopus niveus, Rhizopus japonicus, Rhizopus javanicus*; porcine pancreas lipase, wheat germ lipase, bovine pancreas lipase, pig liver esterase. Preferably, use is made of an enzyme from *Pseudomonas cepacia, Pseudomonas* sp., *Burkholderia cepacia*, porcine pancreas, *Rhizomucor miehei, Humicola lanuginosa, Candida rugosa* or *Candida antarctica* or subtilisin. Such enzymes can be obtained using commonly known technologies and/or are commercially available.

The salt of formula 7 may be converted into the corresponding ester of formula 8

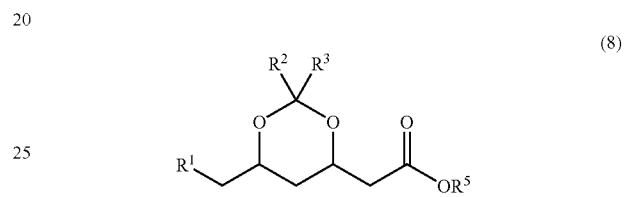

(8)

wherein $R^1$ stands for CN or $CH_2NH_2$, wherein $R^2$ and $R^3$ are as defined above and wherein $R^5$ may represent the same groups as given above for $R^2$, $R^3$ and $R_4$, in a manner known per se (for example as described in WO 02/06266).

For example $R^5$ may represent a methyl, ethyl, propyl, isobutyl or tert butyl group. An important group of esters of formula 8 that can be prepared with the process according to the invention are tert butyl esters ($R^5$ represents tert butyl).

In a special aspect of the invention the salt of formula 7 is converted into the corresponding ester of formula 8 by contacting the salt of formula 7 in an inert solvent, for example toluene, with an acid chloride forming agent to form the corresponding acid chloride and by contacting the formed acid chloride with an alcohol of formula $R^5OH$, wherein $R^5$ is as defined above, in the presence of N-methyl morpholine (NMM).

The acid chloride forming agent can be chosen from the group of reagents that is generally known as such. Suitable examples of acid chloride forming agents include oxalyl chloride, thionyl chloride, $PCl_3$, $PCl_5$, and $POCl_3$. Preferably the acid chloride forming agent is used in an excess relative to the amount the salt of formula 7, for instance between 1 and 3 equivalents, more preferably between 1.2 and 1.8 equivalents.

If desired, in the acid chloride formation also a catalyst may be present. The amount of catalyst may for instance vary from 0-1, preferably 0-0.5 equivalents, calculated with respect to the amount of salt of formula 6. Higher amounts of catalyst are also possible, but will normally have no extra advantageous effect. Preferably the amount of catalyst, if any, will be between 0.05 and 0.2 equivalents calculated with respect to the salt of formula 7. Suitable catalysts are the catalysts generally known to accelerate acid chloride formation, for instance dimethylformamide (DMF) and N-methylpyrrolidone (NMP).

The amount of alcohol of formula $R^5OH$ is not very critical in the conversion of the salt of formula 7 and preferably is between 1 and 15 equivalent calculated with respect to the amount of salt of formula 7, more preferably between 2 and 13, most preferably between 3 and 6.

In practice, in the conversion of the salt of formula 7, in this special aspect of the invention, a small amount of NMM, efficient to catch eventually remaining free HCl, for instance 1.5 to 2.5, preferably 1.8 to 2.0 equivalents calculated with respect to the amount of salt of formula 7 is applied. When a large excess of acid chloride forming agent is used, preferably higher amounts of NMM are used, and when a lower excess of acid chloride forming agent is used, preferably lower amounts of NMM are used.

The salt of formula 7 is preferably contacted with the acid chloride forming agent at a temperature between −30° and 60° C., more preferably between 20 and 50° C. The conversion of the acid chloride into the ester of formula 7 preferably is carried out at a temperature between 20 and 80° C., more preferably between 20 and 50° C.

The conversion of the salt of formula 7 into the corresponding ester of formula 8 according to this special aspect of the invention may be carried out in one step. Preferably first the salt of formula 7 is converted into the corresponding acid chloride, and subsequently the acid chloride is contacted with the alcohol of formula $R^5OH$ and NMM. In a particularly preferred embodiment the acid chloride formed is quenched with NMM and the alcohol of formula $R^5OH$.

The compounds with $R^1$ stands for CN as mentioned herein may be reduced with a suitable reducing agent to form the corresponding compound with $R^1$ stands for $CH_2NH_2$. Suitable reducing agents are the reducing agents known to the person skilled in the art to be applicable in the reduction of a nitrile to an amine and examples of such reducing agents are given above.

It is also possible to start from an enantiomerically enriched compound of formula 2 to prepare the corresponding enantiomerically enriched compounds. An enantiomerically enriched compound of formula 2 may for instance, be obtained by an aldol condensation between acetaldehyde and an aldehyde which is substituted on the 2-position by X in the presence of DERA from *Escherichia coli* as described above.

Starting from (4R, 6S)-6-chloromethyl-tetrahydro-pyran-2,4-diol, via cyanation of its oxidized form (4R, 6S)-6-chloromethyl-4-hydroxy-tetrahydro-pyran-2-one to form the corresponding ((2R,4R)-4-hydroxy-6-oxo-tetrahydro-pyran-2-yl)-acetonitrile and subsequent acetalisation of ((2R, 4R)-4-hydroxy-6-oxo-tetrahydro-pyran-2-yl)-acetonitrile, an ester of ((4R, 6R)-6-cyanomethyl-2,2-dimethyl-[1,3]dioxan-4-yl)-acetic acid, for instance its methyl ester, its ethyl ester or its tert-butyl ester, may be formed. Preferably, the enantiomeric excess (e.e.) of the obtained enantiomerically enriched compounds is >80% ee, more preferably >90% ee, even more preferably 95% ee, even more preferably >98% ee, most preferably >99% ee.

If in the conversion of the ester of ((4R, 6R)-4-hydroxy-6-cyanomethyl-2,2-dimethyl-[1,3]dioxan-4-yl)-acetic acid to the corresponding salt, an enantioselective enzyme is used, even further enantiomer enrichment is realized during the hydrolysis.

The compounds prepared according to the process of the invention are particularly useful in the preparation of an active ingredient of a pharmaceutical preparation, for example of a statin. A particularly interesting example of such a preparation is the preparation of Atorvastatin calcium as described by A. Kleemann, J. Engel; pharmaceutical substances, synthesis, patents, applications 4th edition, 2001 Georg Thieme Verlag, p. 146-150.

The invention therefore also relates to the novel intermediates in such preparation e.g. the compounds (4-hydroxy-6-oxo-tetrahydro-pyran-2-yl)-acetonitrile, 6-(2-amino-ethyl)-4hydroxy-tetrahydro-pyran-2-one, (6-cyanomethyl-2,2-dimethyl-[1,3]dioxan-4-yl)-acetic acid methyl ester, (6-cyanomethyl-2,2-dimethyl-[1,3]dioxan-4-yl)-acetic acid ethyl ester, (6-cyanomethyl-2,2-dimethyl-[1,3]dioxan-4-yl)-acetic acid i-propyl ester, (6-cyanomethyl-2,2-dimethyl-[1,3] dioxan-4-yl)-acetic acid n-propyl ester, [6-(2-amino-ethyl)-2,2-dimethyl-[1,3]dioxan-4-yl]-acetic acid methylester, [6-(2-amino-ethyl)-2,2-dimethyl-[1,3]dioxan-4-yl]-acetic acid ethylester, [6-(2-amino-ethyl)-2,2-dimethyl-[1,3]dioxan-4-yl]-acetic acid i-propylester, [6-(2-amino-ethyl)-2,2-dimethyl-[1,3]dioxan-4-yl]-acetic acid n-propylester.

The invention moreover also relates to a process, wherein a compound obtained in a process according to the invention is further converted into a statin, preferably Atorvastatin or a salt thereof, for instance its calcium salt in a manner known per se. Such processes are well known in the art.

EXAMPLES

Example 1

Preparation of ((2R, 4R)-4-hydroxy-6-oxo-tetrahydro-pyran-2-yl)-acetonitrile (an enantiomerically enriched compound of formula 1)

In a 250 mL 3-necked round-bottom flask equipped with a dropping funnel, a mechanical stirrer and water-bath cooling, 42 g (4R, 6S)-6-chloromethyl-4-hydroxy-tetrahydro-pyran-2-one (an enantiomerically enriched compound of formula 2 wherein X=Cl) were suspended in demineralised water (25 mL) with stirring. An aqueous potassium hydroxide solution (28 g, 50% w/w) was added dropwise over a period of three hours. The dropping funnel was rinsed with water (4 mL) and removed. Solid potassium cyanide (26 g) was added at once and the flask was warmed to 45° C. (water-bath temperature) for 5 h and subsequently to 50° C. for another 30 min. The water-bath was replaced with an ice-bath, and excess cyanide was removed by addition of copper(II) acetate hydrate (1 mg) and dropwise addition of aqueous hydrogen peroxide (8.1 mL, 50% w/w) over a period of 30 min ($T_{max}$=60° C.). After stirring at 22° C. for 1 h, the mixture was cooled with an ice-bath, antifoam (Sigma type 204, 0.02 mL) was added, and aqueous hydrochloric acid (35 mL, 37% w/w) was added dropwise over a period of 2.5 h. The acidified mixture was filtrated through paper, and the filter cake was washed four times with water (10 mL each). The unified filtrate was continuously extracted with ethyl acetate for one day. Another portion of aqueous hydrochloric acid (3 mL, 37% w/w) was added to the aqueous phase which phase was then further extracted continuously with ethyl acetate for two days. The unified organic phases were dried over sodium sulphate, filtered and evaporated in vacuo, leaving a highly viscous orange oil that comprised the target compound ((2R,4R)-4-hydroxy-6-oxo-tetrahydro-pyran-2-yl)-acetonitrile (an enantiomerically enriched compound of formula 1) according to TLC and NMR analysis. Yield: 29.6 g (76%).

A sample of the crude product (1.0 g) was purified by flash column chromatography (100 mL silica 60, 230-400 mesh, 3 cm diameter column, elution with acetonitrile/dichloromethane 3/7 v/v, 20 mL fraction size) to analyse the compound. The purest fractions were unified and evaporated in vacuo, leaving 0.31 g of the target compound ((2R,4R)-4-hydroxy-6-oxo-tetrahydro-pyran-2-yl)-acetonitrile in form of a white solid after drying in high vacuum.

$^1$H-NMR (300 MHz, $d_6$-DMSO, residual undeuterated solvent as internal standard: 2.51 ppm): δ=1.72-1.81 (m, 1H, H-3), 1.88-1.97 (m, 1H, H-3), 2.44 (d"t", J=17.5, ~2 Hz, 1H, H-5), 2.70 (dd, J=17.5, 4.7 Hz, 1H, H-5), 2.95 (dd, J=17.1, 6.6 Hz, 1H of $CH_2CN$), 3.05 (dd, J=17.1, 4.6 Hz, 1H of $CH_2CN$), 4.15-4.21 (m, 1H, H-4), 4.77-4.87 (m, 1H, H-2), 5.37 (d, J=3.4 Hz, 1H, OH).

$^{13}$C-NMR: (75.5 MHz, $d_6$-DMSO, deuterated solvent as internal standard: 39.5 ppm): δ=23.5 ($CH_2CN$), 33.9, 38.2 (C-3/C-5), 60.9 (C-4), 71.05 (C-2), 117.2 (CN), 169.3 (C-6).

Elemental analysis calculated (%) for $C_7H_9NO_3$ (155.15): C, 54.19; H, 5.85; N, 9.03; found: C, 54.4; H, 5.8; N, 9.0.

$^1$H-NMR and elemental analysis results prove that the compound formed is ((2R,4R)-4-hydroxy-6-oxo-tetrahydro-pyran-2-yl)-acetonitrile.

Example 2

Preparation of ((4R, 6R)-6-cyanomethyl-2,2-dimethyl-[1,3]dioxan-4-yl)-acetic acid methyl ester (an enantiomerically enriched compound of formula 6 wherein $R^1$=CN and $R^2$=$R^3$=$R^4$=Me)

A round-bottom flask equipped with a reflux condenser and a magnetic PTFE-coated stir bar was charged with 0.56 g crude ((2R,4R)-4-hydroxy-6-oxo-tetrahydro-pyran-2-yl)-acetonitrile as obtained in Example 1. 2,2-dimethoxypropane (3 mL) and p-toluenesulphonic acid hydrate (15 mg) were added, and the mixture was heated to reflux for 5 h. Another portion of p-toluenesulphonic acid hydrate (15 mg) was added, and heating was continued for another 5 h. After cooling to ambient temperature, the mixture was diluted with ethyl acetate (30 mL) and washed with aqueous sodium bicarbonate solution (5% w/w). The phases were separated, and the aqueous phase was extracted with ethyl acetate (30 mL). The unified organic phases were washed with aqueous saturated sodium chloride solution, dried over sodium sulphate, filtered, and evaporated in vacuo, leaving a yellow oil that comprised the target compound ((4R, 6R)-6-cyanomethyl-2,2-dimethyl-[1,3]dioxan-4-yl)-acetic acid methyl ester (an enantiomerically enriched compound of formula 6 wherein $R^1$=CN and $R^2$=$R^3$=$R^4$=Me) according to TLC and NMR analysis. Yield: 0.37 g (45%).

$^1$H-NMR (300 MHz, $CDCl_3$, residual undeuterated solvent as internal standard: 7.26 ppm): δ=1.12-1.38 (m, 1H, H-5) superposed on 1.36 (s, 3H, Me), 1.44 (s, 3H, Me), 1.75 (d"t", J=12.6, ~2 Hz, 1H, H-5), 2.39 (dd, J=15.7, 6.1 Hz, 1H of $CH_2CN$), 2.49 (center of AB-system, 2H, $CH_2COOMe$) superposed on 2.56 (dd, J=15.7, 6.9 Hz, 1H of $CH_2CN$), 3.67 (s, 3H, $COOCH_3$), 4.13 ($m_c$, 1H, H-6), 4.31 ($m_c$, 1H, H-4).

$^{13}$C-NMR: (75.5 MHz, $CDCl_3$, deuterated solvent as internal standard: 77.2 ppm): δ=19.6 (Me), 24.9 ($CH_2CN$), 29.7 (Me), 35.3, 40.8 (C-5/$CH_2COOMe$), 51.7 ($COOCH_3$), 65.0, 65.4 (C-4/C-6), 99.6 (C-2), 116.8 (CN), 171.0 (COOMe).

$^1$HNMR and $^{13}$C-NMR results prove that the compound formed is ((4R, 6R)-6-cyanomethyl-2,2-dimethyl-[1,3]dioxan-4-yl)-acetic acid methyl ester.

Example 3

Preparation of ((2R,4R)-4-hydroxy-6-oxo-tetrahydro-pyran-2-yl)-acetonitrile on a larger scale than example 1

In a 250 ml 3-necked round bottom flask equipped with a dropping funnel, a mechanical stirrer and a thermometer 50 g (4R, 6S)-6-chloromethyl-4-hydroxy-tetrahydropyran-2-one were suspended in demineralised water (30 ml) with stirring. An aqueous potassium hydroxide solution (34 g, 50% w/w) was added dropwise over a period of two hours. The dropping funnel was rinsed with water (4 ml) and removed. During the addition the temperature of the reaction mixture rose from 25° C. to 35° C. After stirring for additional 45 min solid potassium cyanide (35.6 g) was added at once. Within two hours the temperature of the reaction mixture rose from 30° C. to 65° C. (no external cooling or heating applied). Subsequently the temperature of the reaction mixture was kept between 50 and 55° C. (with an oil bath) for additional two hours.

External heating was stopped and the reaction mixture was stirred at room temperature over night.

The thermometer was replaced by a gas-outlet leading to a wash bottle filled with 50% w/w KOH (to scrub the excess cyanide). Via a dropping funnel aqueous hydrochloric acid (42 ml, 37% w/w) was added over two hours while applying a slight nitrogen overpressure. The pH of the reaction mixture was 3 at the end of the addition. Afterwards the reaction mixture was purged for six hours with nitrogen to remove excess HCN.

The acidified mixture was filtrated through paper and the filter cake was washed four times with water (10 ml each). The unified filtrate was continuously extracted with ethyl acetate for one day. Another portion of aqueous hydrochloric acid (1 ml, 37% w/w) was added to the aqueous phase which phase was then further extracted continuously with ethyl acetate for two days. The unified organic phases were dried over sodium sulphate, filtered and evaporated in vacuo leaving a highly viscous oil that comprised the target compound ((2R,4R)-4-hydroxy-6-oxo-tetrahydropyran-2-yl)-acetonitrile. Yield: 36 g (76%).

Example 4

Preparation of (4R, 6R)-6-cyanomethyl-2,2-dimethyl-[1,3]dioxan-4-yl)-acetic acid methyl ester on a larger scale than example 2

A round bottom flask equipped with a reflux condenser and a magnetic PTFE-coated stir bar was charged with 19 g crude ((2R,4R)-4-hydroxy-6-oxo-tetrahydropyran-2-yl)-acetonitrile as obtained in example 1. 2,2-dimethoxypropane (133 ml) was added and the mixture was heated to reflux (solubility of substrate was poor at low temperatures). p-toluenesulphonic acid hydrate (0.5 g) was added, and heating was continued for three hours. After cooling to ambient temperature the mixture was diluted with ethyl acetate and poured into aqueous saturated sodium bicarbonate solution. The phases were separated, and the aqueous phase was extracted three times with ethyl acetate. The unified organic phases were washed with aqueous saturated sodium chloride solution, dried over sodium sulfate, filtered, and evaporated in vacuo leaving an orange oil that was purified by column chromatography on silica (solvent: petroleum ether/MTBE gradient from 5+1 to 1+1). The resulting yellow oil comprised the target compound ((4R, 6R)-6-cyanomethyl-2,2-dimethyl-[1,3]-dioxan-4-yl)-acetic acid methyl ester. Yield: 12.7 g (46%)

Example 5

Preparation of Sodium ((4R, 6R)-6-cyanomethyl-2,2-dimethyl-[1,3]dioxan-4-yl)-acetate (an enantiomerically enriched compound of formula 7 wherein $R^1$=CN, $R^2$=$R^3$=Me, Y=Na)

A round bottom flask equipped with a magnetic PTFE-coated stir bar was charged with 6.4 g ((4R, 6R)-6-cyanomethyl-2,2-dimethyl-[1,3]-dioxan4-yl)-acetic acid methyl ester as obtained in example 4, toluene (10 ml), methanol (450 mg) and water (6 ml). Sodium hydroxide solution (32 w/w %, 3.9 g) was added dropwise over 10 minutes at room temperature. The resulting two phase mixture was stirred at room temperature for four hours. The toluene phase was separated and discarded and most of the aqueous layer was evaporated in vacuo. The crude residue was used for the following reaction.

Example 6

Preparation of ((4R, 6R)-6-cyanomethyl-2,2-dimethyl-[1.3]-dioxan-4-yl)-acetic acid chloride The crude residue (pH>9) from example 5 was transferred to a round bottom flask equipped with a magnetic PTFE-coated stir bar and a Dean Stark trap. The residue was dried by azeotropic distillation with toluene. At the end of the drying process 100 ml toluene was left with the solid sodium salt. The Dean Stark trap was removed. Oxalylchloride (3.5 ml) was added dropwise via a syringe over 2.5 hours at room temperature while a permanent nitrogen flow through the flask was maintained. After the addition was finished, the reaction mixture was stirred at room temperature for an additional four hours. The orange suspension that had formed was used in the following step.

Example 7

Preparation of 1,1-Dimethylethyl ((4R, 6R)-6-cyanomethyl-2,2-dimethyl-[1,3]-dioxan-4-yl)-acetate (an enantiomerically enriched compound of formula 8 wherein $R^1$=CN, $R^2$=$R^3$=Me, $R^5$=tert butyl)

A round bottom flask equipped with a magnetic PTFE-coated stir bar was charged with tert-butanol (10 ml) and N-methylmorpholine (8 ml). To this solution the toluene suspension was added at room temperature over 30 minutes. The resulting dark brown solution was stirred at room temperature for 12 hours. After dilution with toluene the organic layer was washed three times with aqueous saturated sodium bicarbonate solution, once with aqueous saturated ammonium chloride solution and once with aqueous saturated sodium chloride solution. The organic layer was dried with sodium sulfate, filtered, and evaporated in vacuo leaving 7 g of a dark viscous oil, that was purified by column chromatography on silica (solvent: petroleum ether/ethyl acetate 8+1). The resulting solid comprised the target compound ((4R, 6R)-6-cyanomethyl-2,2-dimethyl-[1,3]-dioxan-4-yl)-acetic acid tert butyl ester. Yield: 3.3 g (43%) over three steps.

The NMR data of the target compound are identical to literature data published for this compound (EP 1077212).

The invention claimed is:

1. Process for the preparation of a compound of formula 1

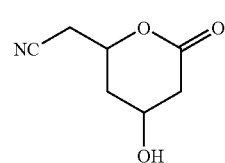

(1)

wherein a compound of formula 2

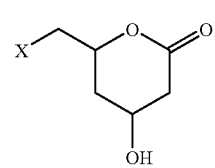

(2)

wherein X stands for a leaving group is reacted with a cyanide ion in water and wherein the pH is subsequently lowered to a pH between 0 and 5.

2. Process according to claim 1, wherein the cyanide ion concentration is at least 1 mole per liter.

3. Process according to claim 1, wherein the molar ratio between the total quantity of cyanide ion and the total quantity of compound of formula 2, is between 0.5 and 10.

4. Process according to claim 1, wherein the compound of formula 1 is first treated with a base prior to being reacted with a cyanide ion.

5. Process according to claim 4, wherein the base is used in a molar ratio of between 0.3 and 3 as compared to the amount of compound of formula 2.

6. Process according to claim 1, wherein the compound of formula 1 is reduced with a suitable reducing agent to form the corresponding compound of formula 3:

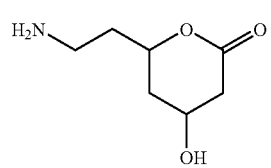

(3)

7. Process according to claim 1, wherein the compound of formula 2, wherein X stands for a leaving group is prepared by an aldol condensation between acetaldehyde and an aldehyde which is substituted on the 2-position by X, wherein X is as defined above, in the presence of an aldolase and by subsequent reaction of the formed compound of formula 4,

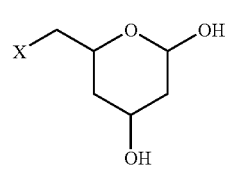

(4)

wherein X is as defined above, with an oxidizing agent.

8. Process according to claim 7, wherein the aldolase used is 2-deoxyribose-5-phosphate aldolase (DERA, EC 4.1.2.4) or a mutant thereof.

9. Process according to claim 1, wherein a compound of formula 1 or a compound of formula 3 is converted into a compound of formula 6,

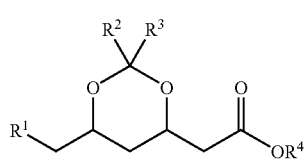

(6)

wherein $R^1$ stands for CN or $CH_2NH_2$ and $R^2$, $R^3$ and $R^4$ each independently stand for an alkyl, an alkenyl, a cycloalkyl, a cycloalkenyl, an aryl or an aralkyl group and wherein $R^2$ and $R^3$ may form a ring together with the C-atom to which they are bound use being made of a suitable acetal forming agent, in the presence of an acid catalyst and wherein the compound of formula 6 with $R^1$ stand for CN is optionally reduced with a suitable reducing agent to form the corresponding compound of formula 6 with $R^1$ stands for $CH_2NH_2$.

10. Process according to claim 9, wherein a compound of formula 6, wherein $R^1$ stands for CN or $CH_2NH_2$ and wherein $R^2$, $R^3$ and $R^4$ are as defined above is subsequently hydrolysed in the presence of a base and water to form the corresponding salt of formula 7,

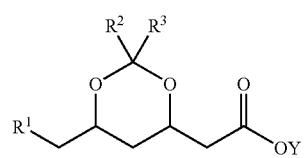

(7)

wherein Y stands for an alkali metal or a substituted or unsubstituted ammonium group, optionally followed by conversion of the salt of formula 7 to the corresponding acid (the compound of formula 7, wherein Y stands for H) and wherein the salt or acid of formula 7 with $R^1$ stands for CN is optionally reduced with a suitable reducing agent to form the corresponding salt or acid of formula 7 with $R^1$ stands for $CH_2NH_2$.

11. Process according to claim 10, wherein the salt of formula 7 or the acid of formula 7 is converted into the corresponding ester of formula 8

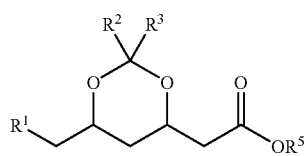

(8)

wherein $R^1$ stands for CN or $CH_2NH_2$, wherein $R^2$ and $R^3$ are as defined above and wherein $R^5$ may represent the same groups as given above for $R^2$, $R^3$ and $R^4$, in a manner known per se.

12. Process according to claim 11, wherein the salt of formula 7 is converted into the corresponding ester of formula 8 by contacting the salt of formula 7 in an inert solvent with an acid chloride forming agent to form the corresponding acid chloride and by contacting the formed acid chloride with an alcohol of formula $R^5OH$, wherein $R^5$ is as defined above, in the presence of N-methyl morpholine (NMM), and wherein the salt or acid of formula 7 with $R^1$ stands for CN is optionally reduced with a suitable reducing agent to form the corresponding salt or acid of formula 7 with $R^1$ stands for $CH_2NH_2$.

13. Process according to claim 7, wherein the compound with a nitrile group ($R^1$ stands for CN) is reduced with a suitable reducing agent to form the corresponding compound with an amine group ($R^1$ stands for $CH_2NH_2$).

14. Process according to claim 1, wherein the obtained compound is enantiomerically enriched.

15. Process according to claim 1, wherein the obtained compound is further converted into statin, preferably Atorvastatin or its calcium salt in a manner known per se.

* * * * *